United States Patent [19]
Ritter et al.

[11] Patent Number: 5,538,738
[45] Date of Patent: Jul. 23, 1996

[54] RETARD SYSTEMS FOR THE SUSTAINED RELEASE OF MEDICINAL AND/OR BIOLOGICAL VALUABLE MATERIALS FROM A DEPOT CARRIER MATERIAL

[75] Inventors: Wolfgang Ritter, Haan; Rudolf Lehmann, Leichlingen; Rainer Sorg, Düsseldorf, all of Germany

[73] Assignee: Henkel Kommanditgesellschaft auf Aktien, Duesseldorf, Germany

[21] Appl. No.: 133,205
[22] PCT Filed: Apr. 11, 1992
[86] PCT No.: PCT/EP92/00825
§ 371 Date: Oct. 18, 1993
§ 102(e) Date: Oct. 18, 1993
[87] PCT Pub. No.: WO92/18108
PCT Pub. Date: Oct. 29, 1992

[30] Foreign Application Priority Data

Apr. 17, 1991 [DE] Germany .................. 41 12 464.2

[51] Int. Cl.$^6$ .................. A61K 47/34; A61K 9/10; A61K 9/14
[52] U.S. Cl. .................. 424/486; 424/434; 424/435; 424/501; 424/DIG. 13; 428/480
[58] Field of Search .................. 424/486, 434, 424/435, 472, 497, 501

[56] References Cited

U.S. PATENT DOCUMENTS 4,322,398  3/1982  Reiner et al. .................. 424/426
4,626,310 12/1986  Ritter .................. 424/78.31

*Primary Examiner*—Edward J. Webman
*Attorney, Agent, or Firm*—Wayne C. Jaeschke; John E. Drach; Daniel S. Ortiz

[57] ABSTRACT

The invention relates to the use of free radical-reactive cross-linker components based on olefinically unsaturated esters of lower hydroxycarboxylic acids and/or oligomers thereof for modifying depot materials, and especially retard systems, which contain medicinal and/or biological valuable materials in admixture with a carrier material in a sustained release form. The cross-linkers are present as polymer compounds in the application form of the retard system and may be provided in the retard system or depot material to be applied in a largely homogeneous as well as in a non-uniform distribution. The invention also relates to retard systems which contain medicinal and/or biological valuable materials and have been based on oligomer and/or polymer compounds of lower hydroxycarboxylic acids as carrier materials providing a sustained release of the active substance. The retard systems and/or depot materials are modified with polymer compounds prepared from olefinically unsaturated esters of lower hydroxycarboxylic acids and/or oligomers thereof.

21 Claims, No Drawings

RETARD SYSTEMS FOR THE SUSTAINED RELEASE OF MEDICINAL AND/OR BIOLOGICAL VALUABLE MATERIALS FROM A DEPOT CARRIER MATERIAL

This application is a 371 of PCT/EP92/00825 filed Apr. 11, 1992.

BACKGROUND OF THE INVENTION

1. Field of the Invention

The invention relates to a development in the field of sustained release systems of active substances, more particularly in the area of medicinal and/or biological valuable materials from a carrier material.

2. Statement of Related Art

Combination materials of this kind are the subject matter of numerous recent investigations and printed publications in both the fields of pharmaceutical auxiliary materials and of biological preparations, for example crop protection chemicals. They are designated by terms such as retard systems, depot or slow release materials, respectively, or quite generally as mixtures of active substances providing a sustained release of the valuable materials.

Depot materials of this kind usually consist of a carrier with or without any activity of its own, in which an active substance, the release of which is to be sustained, has been incorporated. In recent literature particular attention has been given to polymer compounds based on polyesters of lower hydroxycarboxylic acids as carrier materials, more specifically those having from 2 to 6 carbon atoms in the hydroxycarboxylic acid molecule. Carrier materials of this kind are prone to undergo hydrolysis and are subject to biological degradation mechanisms. The corresponding polyesters derived from glycolic acid, lactic acid and/or hydroxybutyric acid having restricted molecular weights are of particular importance.

Among the more recent pertinent literature, reference may be made, for example, to U.S. Pat. No. 4,011,312, which discloses solid formulations of copolyesters of glycolic acid and lactic acid, having molecular weights of below 2,000, as a carrier material in admixture with antibiotically active substances such as tetracycline, neomycin and other antibiotics for the treatment of bovine mastitis at room temperature or body temperature. The preparation of lower molecular weight poly($\beta$-hydroxybutyrate, PHB) and the use thereof as a solid carrier material for the formulation of sustained release tablets containing a pharmaceutically active substance has been described in "Die angewandte makromolekulare Chemie" 161 (1988), 1–8 (No. 2604). Upon the investigation of the release kinetics it has been shown, in the case presented here, that the amount of the active ingredient released is highly dependent on the molecular weight of the PHB fraction, the retardation in the release of the active substance being increased with the decrease in the molecular weight.

Numerous investigations deal with the use of resorbable polyesters based on glycolic acid/lactic acid as a carrier material for the sustained release of the active substance when used in combination with medicinal valuable materials, crop protection agents and the like. Reference may be made, e.g., to D. L. Wiese et al. in: "Drug Carriers in Medicine", Academic Press, London 1979, pp. 237–270, and to the literature quoted therein re retard forms of drugs; R. L. Kronenthal, Polym. Sci. Technol. 1975, 8 (Polym. Med. Surg.), 119–137.

The manner of the release of the active substance is affected, on the one hand, by the interaction between the active substance and the carrier material while, on the other hand, it is highly dependent on the structure and the properties of the usually polymeric carrier material. For example, the active substance may be micro-encapsulated in the polyesters of the type mentioned, it may be embedded in the polymer matrix, or it may be bonded to the terminal groups.

Thus, the release of the active ingredient proceeds via different mechanisms depending on the formulation. In the case of encapsulated active substances the diffusion of the active substances through micropores in the envelope plays an important role. If the active substances are dispersed or dissolved in a solid polymer matrix, the release of the active ingredients is governed by the diffusion through the matrix, by the hydrolytic erosion of the matrix or by a combination of these parameters. Nevertheless, the usability of such a depot system includes considerations on how the concerned substance mixture is to be handled. The depot material should be storage-stable under normal conditions of storage, should be sufficiently solid and dispensable in portions, should not undergo clogging during the conditions of manufacture, transportation and storage, and should exhibit a sufficient stability to the presence of moisture and the like.

In consideration of these numerous requirements which are difficult to reconcile with each other, it is not unusual that to date, use of retard systems and/or depot materials based on body-resorbable polyesters of lower hydroxycarboxylic acids have not been used in practice.

BRIEF DESCRIPTION OF THE INVENTION

It is the object of the invention to advance the development of retard systems and/or depot materials, of the described type, in such a way that the final product may be optimally adapted to the application. The invention provides the elements, described in detail hereinbelow, for providing the depot material in the form of a module system, which elements provide a degree of freedom, so far unknown, for providing a combination of properties necessary in the final product in response to the profile of required properties.

The invention, in a first embodiment, relates to the concomitant use of free radical-reactive components, based on olefinically unsaturated esters of lower hydroxycarboxylic acids and/or oligomers thereof, for modifying depot systems, and especially retard systems, which contain medicinal and/or biological valuable materials in admixture with a carrier material in a sustained release form of the active substance(s). Said reactive components are present as polymer compounds in the application form of the retard system and may be provided in the retard system or depot material to be applied in a largely homogeneous as well as in a non-homogenous distribution.

Accordingly, the invention further relates to retard systems which contain medicinal and/or biological valuable materials mixed with oligomer and/or polymer compounds of lower hydroxycarboxylic acids as carrier materials which provide sustained release of the active substance. The invention is characterized in that said retard systems and/or depot materials have been modified with polymer compounds prepared from olefinically unsaturated esters of lower hydroxycarboxylic acids and/or oligomers thereof. These olefinically unsaturated esters of lower hydroxycarboxylic acids and/or oligomers thereof which do form polymer compounds, within the scope of the teaching of the invention, will be designated, for the sake of simplicity, also as "cross-linkers" or "cross-linker components" within this description of the invention.

DETAILS OF THE INVENTION

The system of the invention will be described by sustained release carrier/valuable material mixtures which are designed to be used with humans and/or animals. The mixtures contain antibiotically active substances; and more particularly, broad-spectrum antibiotics, in a carrier material which is derived from lower hydroxycarboxylic acids; especially from lactic and/or glycolic acids, and is resorbable by the body. The combination material, which is described in detail by way of examples hereinbelow, is tissue-compatible so that its incorporation in a living body will be possible. Said combination material is of particular importance as a retard system, which releases an antibiotic with some retardation, and sustains said release for a sufficiently long period upon implantation of the multi-component material, according to the invention, into human or animal living tissue. Thus, this retard material, within the scope of the invention, is suitable for wound disinfection in surgical procedures as an auxiliary material which is resorbable by the body. The material of the invention is capable of replacing any of the conventional non-resorbable auxiliary means which, for example, ensure a sustained antibiotics release from solids inserted at the surgical site, but which in turn must be removed from the human or animal body.

The exemplifications of the invention by way of the examples, as described herein, does not imply any limitation of the teaching according to the invention. By way of said examples, there are disclosed combinations of elements which act according to the invention and which are applicable to other fields of application in the same manner. More particularly, the invention is applicable to a broad range of valuable materials to be released. For example, other important valuable materials for implantation in the living organism include cytostatics, hormones, insulin, cortisone and the like. Adjustably high local concentrations of the active ingredient are attainable over an extended period of time, with a simultaneous reduction in the total stress on the organism, by embedding the depot material(s) of the invention in the region concerned by the disease or in any other freely chosen region.

The area of application of the retard systems according to the invention in the medical and/or veterinary field, however, is not limited to valuables-containing substance mixtures for direct implantation into living tissue: The invention includes valuables-containing admixtures that are suitable for topical administration to a human or an animal. The term "topical administration" comprises the application of valuable materials to mucosa regions as well as the so-called transdermal administration of valuable materials by applying the preparation to selected areas of the outer skin. In all of these cases the substance mixtures according to the invention are distinguished by the fact that the rate of release of the valuable material is adjustable. This, for example, allows the successful application of valuable materials to the living organism over a pre-determinable period of time at delivery concentrations which are, to a large degree, freely predeterminable. In any particular case it will be necessary, of course, to examine and determine interactions between the structural elements of the retard system within the scope of the invention and the valuable material to be released therefrom, as well as the interaction between the living body and the retard system at the site of application thereof. Nevertheless, the great freedom in the selection of the structural elements in the retard systems according to the invention, and the comparably great freedom in combining said structural elements provides new possibilities for the time-controlled release and application of virtually any valuable material.

More particularly, the invention is suitable for improvements in the field of bioadhesive preparations of active ingredients. Bioadhesive preparations are systems which exhibit increased adhesive strength due to an interaction of functional groups or functional regions, respectively, on the surface of the active substance mixture with mucosa regions of the body with the participation of body fluids, for example, possess an extended residence time in the gastrointestinal tract. As to the term "bioadhesive preparations of substances", we here refer to, e.g., Herve Tournier et al., "New Bioadhesive Polymers for Topic Mucosal Dosage Forms"; Proceed. Intern. Symp. Control. Rel. Bioact. Mater. 15 (1988), Controlled Release Society, Inc., No. 237, pp. 418/419, and the literature quoted therein.

The teaching of the invention discloses a variety of exemplifications of substance mixtures, disclosing the retard system and the adjustment thereof to the parenteral, enteral or other topical application. All of these different substance mixtures, however, are governed by the uniform principles of the invention as discussed in detail hereinbelow.

The carrier material for the sustained release of the active substance(s)

The preferred carrier materials according to the invention are defined as oligomer and/or polymer compounds of hydroxycarboxylic acids having from 2 to 6 carbon atoms, among which the corresponding hydroxycarboxylic acids having from 2 to 4 carbon atoms are of particular importance. Glycolic acid and/or lactic acid are compounds useful in the practice of the invention, which are readily accessible on a commercial scale; the selection of these components plays an important role, due to the different hydrolytic stabilities of the compositions, The useful lactic acid derivatives include the respective components of any steric configuration, i.e. D-, L- and/or DL-forms including the racemates. The rate of decomposition of the polymer compound under the hydrolytic action of metabolic sources is determined in a per se known manner by appropriately selecting the polyester-forming components. Polyglycolic acid is known to be decomposed by hydrolytic degradation within a few days, whereas the decomposition of poly-DL-lactide may require from weeks up to some months.

In recent pertinent publications concerning polymer materials useful in the practice of the invention, crucial importance is attached to adjustment of pre-determined degrees of polymerization which, if possible, are uniform. Reference may be made, for example, to EP-A1-0 244 114 and to EP-A2-0 299 730. Here an attempt to meet the multiform requirement profile of a depot material by the choice and adjustment of selected parameters of the polyester-based carrier material is made.

The teaching according to the invention, of the concomitant use of the above-defined cross-linker components, which are described in detail hereinbelow, as an integral constituent of the depot material, permits free variation of the carrier which is derived from lower hydroxycarboxylic acids, especially lactic and/or glycolic acids. More specifically, when the major component of the carrier is selected, the teaching of the invention, allows said major component to be determined to effect optimization of the sustained release of the valuables under the respective conditions of application. Further elements of the requirement profile of the depot material are generated or satisfied, respectively, in a manner still to be described, by the cross-linker components. Thus, suitable carrier materials for the practice of the invention are generally oligomers and/or polymers of lower hydroxycarboxylic acids having a tough-viscous to solid consistency at room temperature. More particularly, oligoesters having average molecular weights within the range of from about 200 to 5,000 are suitable, wherein preferred oligoester materials have average molecular weights within the range of from about 300 to 2,000.

In the course of the work on which the present invention is based, it has surprisingly been shown that, in combination with antibiotics, useful release rates of the active substances can be achieved, when the major portion of the carrier substance is based on bone waxes such as described in the printed publications DE 32 29 540 (now U.S. Pat. No. 5,277,900), DE 37 16 302 (now U.S. Pat. No. 5,236,702) and DE 38 25 211 (now U.S. Pat. No. 5,143,730), the disclosures of which US patents concerning the nature of the tough-viscous to solid waxy polyester oligomers are incorporated by reference in the present disclosure in the context of the carrier material for providing sustained release of the active substance.

DE 32 29 540 (now U.S. Pat. No. 5,277,900) describes resorbable waxes for mechanically stopping bleeding in endogenous hard tissue, prepared from said lower hydroxycarboxylic acids, more particularly glycolic acid and/or the lactic acid. These waxes, due to their structures, are degradable by endogenous metabolic mechanisms. The rate of degradation is controllable in a known manner. Oligomers of glycolic acid are decomposed faster than those of lactic acid by the endogenous metabolism. The preferred waxes exhibit average molecular weights within the range of from about 200 to 1,500, and more specifically within the range of from about 300 to 1,000.

For controlling the average molecular weight of said polyester oligomers it is proposed to concomitantly use mono-functional and/or polyfunctional alcohols or carboxylic acids. Then an average molecular weight can be pre-determined in a known manner by choosing suitable mixing ratios of the hydroxycarboxylic acid and the additional monofunctional and/or polyfunctional component(s). The resulting reaction products still contain some amounts of the starting components employed.

DE 37 16 302 (now U.S. Pat. No. 5,236,702) describes optimization of these waxy polyesters. Here, it is disclosed that a definite trifunctional alcohol, viz. glycerol, is employed for adjusting the average molecular weight. The combination of glycerol with oligoesters of lactic acid and/or of glycolic acid results in degradable wax-like components, which when implanted into tissue of the living body are distinguished by a well pronounced compatibility with the body. In order to exclude any undesirable tissue damage, purification of the degradable wax may be provided to remove unreacted carboxyl groups.

The body-resorbable tough-viscous to solid waxes of DE 38 25 211 (now U.S. Pat. No. 5,143,730) which are based on oligomers of glycolic acid and/or lactic acid, and are distinguished by a content of body-compatible salts of organic and/or inorganic acids, which salts have been formed by the reaction of the free carboxyl groups possibly present in the oligomer wax and/or have been incorporated in the wax by homogeneous distribution of added salts. Particularly suitable as admixed components are alkali metal, alkaline earth metal and/or aluminum salts, among which the salts of sodium, calcium and/or magnesium are of particular importance.

In a preferred embodiment of the invention, oligomeric waxes of low molecular weights are employed as the carrier materials. Waxes of this kind based exclusively on glycolic acid, as the lower hydroxycarboxylic acid, undergo rapid decomposition in the body so that only a short period of sustained release of the valuables can be assured. This effect may be deliberately utilized according to the invention. Under some aspect: The incorporation in the retard system, of such proportions of glycolic acid-based wax, results in release of valuables in controllable amounts in the initial phase of the period of action. Thus, in surgical practice it may be desirable to assure local availability of a comparably high cocentration of antibiotics. The addition of adequate amounts of some rapidly decomposing glycolic acid wax filled with the pre-determined antibiotic would satisfy this need.

However, an exclusive glycolic acid-based wax is not suitable for the release of an antibiotically active substance over an extended period of time, for example over a period of from two to four weeks. Applicants' investigations have shown that lactic acid waxes having low molecular weights are distinguished by providing an extended rate of valuable-release. Thus, lactic acid oligomers having average degrees of oligomerization of from about 6 to 20 lactic acid units per molecule, and especially those comprising from about 8 to 15 lactic acid units per molecule, are particularly suitable for assuring a local uniform release of antibiotics for the period of from about 1 to 4 weeks after implantation into living tissue. For this application, appropriate lactic acid waxes can be prepared in a particularly simple manner by the concomitant use of polyfunctional alcohols. The glycerol esters of lactic acid having an average of from 3 to 5 lactic acid units per oligoester moiety, which are especially mild to the body, can be used with particular advantage. As to a use of ethyleneglycol, the average molecular weights of the oligo-lactic acid moieties are applicable.

Investigations on the degradation behavior of oligoesters of the kind described here revealed that the respective lactic acid-based glycerol waxes may possess considerable resistance to hydrolytic degradation so that the absorption thereof in the living organism may take substantially more time than the sustained release period of the pharmacologic valuable material. This fact is irrelevant to the usability of this carrier material within the objective of the invention. If in an individual case this retarded degradation of the carrier material based on lactic acid/glycerol is detrimental, then opposite controls may be used such as a binary mixture of glycolic acid-based and lactic acid-based proportions of wax and which will be described hereinbelow.

The comparably low molecular weight waxes and more particularly lactic acid-based waxes, however, fail to meet requirements of the properties of such a depot material in relation to handling, non-tackiness, storage stability and the like. This drawback, inherent to said waxes, is entirely overcome according to the teaching of the invention. The deficiencies in the properties can be compensated for by the concomitant use of the previously defined cross-linker components as will be explained hereinbelow.

The considerations with respect to the selection and nature of certain preferred carrier materials, for the immediate implantation into living tissue, are also applicable to retard systems for the enteral and/or topical application. However, here the ranges of suitable representatives of the carrier material, within the scope of the invention, are reasonably enlarged. This may be illustrated by way of the following example: Upon an oral application, the presence of free carboxyl groups in the carrier material is tolerable; for the mechanism of bioadhesion, the interaction of the mucosal areas with functional carboxyl groups on the surface of the administered multicomponent mixture is a known and important mechanism leading to a sustained bonding of the applied multicomponent mixture to the respective mucosal areas. Thus, carboxymethyl cellulose and/or polymer or copolymer compounds of acrylic acid and/or methacrylic acid, having free carboxyl groups, are important known polymeric carriers for bioadhesive preparations of active substances of the kind of interest here.

According to the invention, by way of appropriately designing the carrier material, this known mechanism for the mucosal interaction can be complied with by using monovalent and/or preferably polyvalent carboxylic acids for the regulation of the average degree of oligomerization of the hydroxycarboxylic acid esters. Then, the resulting oligomer molecule is characterized by the presence of terminal carboxyl groups, which upon the application in the finished product, may enter into bioadhesive interaction with the mucosal areas. Physiologically acceptable representatives are especially suitable as the molecular weight-controlling carboxylic acid, among which, the edible acids are examples which are known to include the range of useful mono- and polyvalent carboxylic acids.

In regard to the question of the stability to hydrolytic degradation, the considerations set forth above, in the context of the selection of the defined hydroxycarboxylic acids for synthesizing the oligomeric carrier materials are applicable in the same manner.

The cross-linker components employed according to the invention

The components described as cross-linker components in the following are free radical-reactive components which preferably are polyfunctional and can be reacted via olefinic double bonds to form polymer compounds. In the ready-to-use depot material the reactive cross-linkers have been converted into the corresponding polymer compounds by polymerization and/or cross-linking and, in these forms, determine important material properties of the depot material. They have particular importance inter alia for the consolidation of the total composition which contains the carrier materials based on tough-viscous to waxlike oligomer compounds as the major component. Surprisingly it has been shown that soft waxes may be turned into sufficiently solid, non-tacky or even tack-free materials by small amounts of such reactive constituents. More specifically, an in situ curing of the cross-linker components in admixture with the respectively selected wax-based carrier material will lead to combination materials which encompass the whole spectrum of the required application-technological properties. The working principle of the invention includes a plurality of examples of the final product which will be discussed hereinbelow.

The reactive cross-linkers useful according to the invention and/or the polymer compounds formed thereof by way of reaction are based on olefinically unsaturated esters of lower hydroxycarboxylic acids and/or oligomers thereof. By use of the unsaturated esters of hydroxycarboxylic acids the degradation of the implanted polymer compounds and the resorption of this component can be assured.

Suitable for the use as cross-linker components, are polyfunctional components which comprise more than one functional olefinic group in the molecule. Especially suitable are di- to tetrafunctional olefinically reactive hydroxycarboxylic acid oligomers which comprise at least a substantial proportion of the cross-linker components.

Preferred cross-linkers according to the invention are esters and/or oligoesters of lower polyfunctional alcohols or carboxylic acids with lactic acid and/or glycolic acid, which in addition have terminal olefinically unsaturated groups. Particularly suitable cross-linker components are derived from lower di- to tetrahydric alcohols, and more specifically from ethyleneglycol and/or glycerol, which have been olefinically substituted in the terminal positions with acrylic acid and/or methacrylic acid moieties - designated as (meth-)acrylic acid moieties within this description of the invention.

Reactive components useful in the practice of the invention have been described in detail, for example, in DE-A1 32 04 504 (now U.S. Pat. Nos. 4,675,433 and 4,731,425) and DE-A1 32 29 635 (now U.S. Pat. No. 4,626,310). In these references, more specifically, there have been provided (meth)acrylate compounds having terminal (meth)acrylic acid moieties on an oligomer chain of hydroxycarboxylic acids, said compounds being slow-evaporating and liquid to solid at room temperature, wherein the polyester oligomers have an average molecular weight within the range of from 200 to 600. The polyfunctional (meth)acrylic acid esters are intended to be used as surgical binder systems for bonding endogenous hard tissue with plastics and/or metal. Compounds of this kind are suitable examples of cross-linkers according to the invention.

However, reactive cross-linker components are not limited to (meth)acrylic acid esters. The introduction of reactive olefinic groups into an ester molecule of the invention may be effected in any known manner. Reference may be made here, by way of example, to the known introduction of terminal olefinic groups into basic structures containing carboxyl groups. The same considerations are applicable in relation to those carrier materials which in one preferred embodiment are oligomers terminated with hydroxyl groups, while they have been formed as the corresponding carboxyl group-terminated oligomers for certain intended uses for example, for bioadhesive materials. One class of cross-linker components which is especially important for use in living human and animal organisms comprises the reaction products of glycerol esters of lactic acid and/or oligo-lactic acids modified with terminal (meth)acrylic acid moieties. In addition to or in the place of lactic acid, glycolic acid moieties may be incorporated in the cross-linker molecule. In a preferred embodiment, the cross-linkers, as a random average, contain at least two olefinically unsaturated terminal groups, and which cross-linker components have been completely reacted with (meth)acrylic acid and/or the reactive derivatives thereof are a particularly interesting class of cross-linker components within the teaching according to the invention. These cross-linkers comprise, as a random average, from 2 to 3 olefinic terminal groups per one mole of glycerol, in one important embodiment may contain from 3 to 12 moles of lactic acid moieties, and especially from 3 to 6 moles of lactic acid moieties, as a random average per one mole of glycerol. Reactive glycerol derivatives having a molar ratio of glycerol/lactic acid/(meth)acrylic acid of about 1/4/3 are highly effective cross-linker components, which when admixed in an amount of, for example, from 1 to 5% by weight—relative to the weight of the non-reactive carrier material—are capable of modifying the physical nature of a tough-viscous or soft waxy carrier so that it satisfies the requirements of the invention.

The following considerations are relevant to sustained release systems to be implanted into the living body: The teaching according to the invention provides material mixtures, which, with respect to all components thereof, have been optimized to body compatibility. This consideration is especially important with respect to the cross-linker components.

The cross-linkers are systems susceptible to undergo a polymerization reaction via free radicals. Such systems, in order to safely exclude an undesirable premature reaction, require the concomitant use of free radical inhibitors. More particularly, such free radical inhibitors are also needed for the preparation of the free radical-reactive systems such as the polyfunctional (meth)acrylate esters. It is the high gelling tendency of the polyfunctional (meth)acrylic acid esters that requires the use of highly efficient inhibitors in the production process. In accordance with one essential feature of the invention, the concomitantly used cross-linker components are free from inhibitors which as to kind and/or amount are undesirable and would remain in the cross-linker from the production, storage and/or processing of the polyfunctional components.

One particularly important example of a suitable inhibitor according to the invention comprises tocopherol compounds and, among these, more specifically, α-tocopherol and, thus, vitamin E.

The use of physiologically compatible tocopherol compounds, and more specifically of vitamin E, as a polymerization inhibitor, in the preparation of polyfunctional (meth)acrylic acid compounds is the subject matter of Applicants' older application DE 39 39 161 (equivalent to U.S. application Ser. No. 07/859,435), the disclosure of which application is hereby incorporated by reference in the disclosure of this invention.

Within the scope of the teaching of the invention, relevant to the cross-linker components is the disclosure of the quoted older application DE 39 39 161 which describes the use of olefinically reactive (meth)acrylic acid esters which are free from solvents, and more specifically of residual amounts of solvents left from the production. According to a preferred embodiment of the invention, in the preparation of the cross-linker components no solvent is used, more specifically no physiologically questionable solvent is used. In this context reference is made to the disclosures of Applicants' printed publications DE-A1 38 43 854, 38 43 938, 38 43 930 and 38 43 843.

The mixing ratios between the carrier material and the cross-linker components and/or the polymer components formed by the reaction thereof, may vary within wide limits. The mixing ratio is governed by a plurality of parameters, among which the following may be mentioned in particular: Nature of the carrier material, especially its physical nature at room temperature and at the application temperature, profile of the requirements set for the quality and nature of the depot material upon storage and application, reactivity and nature of the cross-linker components and/or of the polymer components formed by the reaction thereof, as well as the profile of requirements set for the final material in view of the intended use. More particularly, it will be readily apparent that materials to be implanted into a living organism, to release pharmaceutical compositions, will have to meet requirements different from those set for a depot material to be used for the sustained release of biologically active substances, for example, in the agricultural sector. As far as the mixing ratios of the non-reactive carrier material, and the reactive carrier components, in general the cross-linker components will comprise not more than half of the entire system. In a preferred embodiment substantially lower amounts of cross-linker components will be used. More specifically, the modifying and at least partially reacted cross-linker components may be present in the mixture in proportions of from about 0.5 to 40% by weight, and preferably in proportions of from about 1 to 10% by weight—% by weight relative to the sum of carrier material and cross-linker components. For a use of the retard systems, according to the invention, in the medicinal sector, and especially for implantation into the living tissue, proportions of the cross-linker components of at most about 10% by weight may be preferred. As has already been mentioned, good results can be obtained with mixing ratios of up to 5% by weight, and especially by using mixtures containing from about 2 to 5% by weight of cross-linker components. Lower proportions are particularly applicable to use of compounds having comparably high cross-linking activity, for example those compounds having three-functional (meth)acrylic acid esters of the hydroxyl-terminated glycerol/lactic acid esters or oligoesters.

The various embodiments of the retard systems

It is difficult to predict the release behavior of retard systems because a variety of interaction parameters will affect the ultimate activity of the system. It is a particular advantage of the invention that it provides an opportunity to meet the profile of requirements set for an individual application by means of varying the examples of the system. This will be understood from the following considerations:

The major portion or at least an essential portion of the depot material is usually comprised of the carrier material as described hereinbefore. The time-control of the release can be influenced by means of the selection of the components forming the oligomer and/or polymer components and the release characteristics dependent thereon. This is applicable to compounds with a known composition. A further modification ensues from use of carrier materials having an at least binary composition combining different wax or resin types. For example, oligomer and/or polymer compounds which undergo a comparably fast degradation, are used in combination with compounds that are subject to a slower degradation. A further option for controlling release characteristics is provided by the manner in which different components of the carrier material are combined. It covers the whole range from homogeneous mixtures through mixtures which combine delimited sectors of a material having a pre-selected composition with corresponding sectors of a material having a different composition and, hence, a different degradation behavior. The form presented here, for example, may control the porosity or the permeability of a block comprising carrier material composition to permeation of body liquid and/or permeation of cell growth. Also a layer-like arrangement of the various components of the carrier material may be taken into consideration to form a primarily continuous material block which in practical use would comply with various requirements, due to the different degradation rates of the individual layered blocks.

The modifications outlined here for modification of the carrier material can be extended by the concomitant use according to the invention of the cross-linker components. The modifications discussed above are applicable to the substance mixtures composed of carrier material and cross-linker components. In one embodiment the carrier material and cross-linker components—together with the valuable materials—may be present as a largely homogeneous mixture. Nevertheless, it is also possible that the cross-linker components and/or the polymer compounds resulting therefrom are present in a layerwise arrangement in the retard system so that regions of the valuable carrier mixture are free from cross-linkers and are interspersed and/or enclosed by reacted cross-linker components. Cross-linker components need not be combined with all of the carrier materials. For example, release-retarding carriers especially those types of lactic acid oligomers which are in a tough-viscous state at room and/or application temperature are interspersed with cross-linker components within the scope of the invention and are fixed such as to be dimensionally stable, for improved handling. Combination materials of this kind may then be mixed with additional carrier materials, for example, those based on polymers having higher molecular weights or the glycolic acid oligomers and/or polymers which are in the solid state.

The possibilities enumerated elucidate the following: Due to the cross-linker components and the ability provided for influencing the nature of the material in those regions of the depot material which are determined by the cross-linker components and/or the polymer compounds produced thereby, it is possible for the first time to put into the intended use comparably low molecular weight carrier materials of hydroxycarboxylic acid oligomers; in many cases it is just these carrier materials having comparably low molecular weights which in many cases exhibit the desirable retarded release characteristics. Hindrances to regenerative cell growth can be reliably excluded since individual regions of the respective carrier materials—for example those based on lactic acid—can be small. The depot material, stabilized according to the invention, may be introduced as a fine granular material or even as a powder into the tissue regions, or it may be employed in topical application forms. It is possible to fix large three-dimensional forms, for example plates, rods, spheres or any other three-dimensional form in the living tissue and, due to the predictable degradation characteristics of such an enlarged volume unit in the living organism exclude undesirable delay of the regenerating cell growth.

Curing of the cross-linker components

In conjunction with the considerations discussed above concerning the possible variety of the depot materials to be designed according to the invention, it will be understood that there is also a number of possible approaches for converting the cross-linker components of the invention into their polymer compounds. It is possible to adapt the invention to a particular use and to reliably provide a depot material which in use makes the valuable materials available in an undegraded form.

Investigations conducted by Applicants have shown that in a broad range of carrier/valuable mixtures it is possible to admix cross-linker components with the carrier/valuable mixture to form a homogeneous mixture and to allow an in situ reaction without inducing substantial damage or deterioration to the valuable material. In this simplest embodiment of the invention the modifying polymer compounds have been prepared in situ from the radical-reactive cross-linker components in admixture with at least one portion of the depot material based on carrier/valuable material. Mixtures of active materials of glycerol/lactic acid-based oligomers as carrier material and aminoglycoside antibiotics may be prepared by melting the carrier material at comparably low temperatures and introducing the valuables to form a homogeneous mixture. For example, temperatures of below or at least within the range of about 70° C. are in fact sufficient for melting said carrier materials. Within the same temperature range, small amounts, for example from 1 to 5%, and especially from 2 to 4% by weight, of cross-linker components based on glycerol/lactic acid/(meth) acrylic acid can be admixed to form a homogeneous mixture. The in situ cross-linking of the cross-linker components is successfully accomplished by means of a free radical-initiated reaction, whereby the corresponding polymer compounds are formed which determine the ultimate characteristics of the depot material designed to release pharmaceutical compositions. For example, shaped articles may be produced which are largely tack-free in the dry state and may be subjected to further comminution, if so desired.

If it appears that there may be danger of interactions between the particular valuable material and the cross-linker components that would cause the characteristic of the valuable material to be impaired, then the principle of the invention can still be applied. In such a case, the carrier/valuable mixtures can be converted into a predetermined particulate form and then provided with an envelope containing cross-linker components within the scope of the invention. Here, mixtures of carrier material and cross-linker components can be employed which are free from valuables within the envelope region. The carrier material used in this case may be the same or different from the carrier material used in the interior region for the valuable to be released. In the subsequent curing step no substantial interaction of the cross-linker components with the valuable material embedded in the core occurs. The two embodiments presented here are understood to be examples of the present invention. The two embodiments may be employed separately or in combination with each other, with further embodiments being derivable for the requirements of a particular depot material and from the numerous possible combinations as described hereinabove.

In one preferred embodiment of the invention the initiation of the polymerization reaction can be performed under conditions which exclude physiologically undesirable components from being introduced into the product. Hereto, reference is made to the indications set forth in the Applicants' German Patent Application P 40 37 516 (U.S. application Ser. No. 08/066,087), the pertinent disclosure is hereby incorporated by reference in the disclosure of the present invention.

In said older Application P 40 37 516 (U.S. Ser. No. 8/066,087) there have been described degradable high-strength materials and shaped articles for implantation into human and animal organisms, which materials are comprised of cured (meth)acrylic acid esters of polyfunctional hydroxy-terminated oligomers of lower hydroxycarboxylic acids. They are characterized in that, inter alia, they are substantially free from reaction aids and/or other additives resulting from the production (contaminants of the active substances) which are undesirable with respect to kind and/or amount. In particular, the production procedure has been effected with respect to kind and amount—of the inhibitors of the polyfunctional (meth)acrylic acid esters and the initiators and/or starter systems used for cross-linking. Curing is to be effected either by radiation curing—especially using UV radiation—or by using starter systems which are based on body-compatible components or have been restricted as to kind and amount so that residual matter released upon the degradation of the system does not give rise to any physiological problems.

Within the scope of radiation curing there may be considered, in addition to curing by UV light as already mentioned, the use of other reaction-inducing types of radiation, for example, laser beams, X-ray or γ-rays. Concomitant use of per se known initiators is possible; in this context, reference is made, for example, to the printed published indications in Encyl. Polym. Sci. and Eng. (2nd edition), Volume 11, 187–207, and pertinent commercial products, available, e.g., from the companies Merck, Darmstadt (DE), and Ciba-Geigy (Switzerland).

According to the invention, it is possible to cure the reactive material in a per se known manner by chemically induced free radical-initiated polymerization. If known auxiliary agents are employed, the following may serve to facilitate the selection of reaction aids: A multiplicity of redox systems based on peroxidic compounds used in combination with reducing agents and/or compounds of metals that occur in several valency states. In this context reference is made, for example, to the survey presented in PROGRESS IN POLYMER SCIENCE, Vol. 8, Pergamon Pres, Oxford-New York, 1982, pp. 61–131, and the voluminous primary literature referred to therein.

In the selection of suitable redox systems which do not give rise to substantial physiological concerns with respect to kind and amount of the residual materials remaining in the reacted material, the following state of facts is particularly useful for preparing compositions within the scope of the invention. Reactant systems which physiologically are comparably safe, have been described in the prior art especially in connection with aqueous polymerization systems. The material to be cross-linked according to the invention is per se an anhydrous system. However, due to its oligomeric structure derived from lower hydroxycarboxylic acids, compounds which are employed in aqueous system can be soluble in compositions of the invention. It can be possible to accomplish a homogeneous distribution of physiologically largely acceptable activator systems in the anhydrous reaction phase of the polyfunctional (meth)acrylic acid esters or of the admixtures thereof with the carrier materials, so that cross-linking can be effected at pre-determined temperatures.

It is only by way of example that from the broad class of suitable components for such redox systems the following may be mentioned here: Peroxide compounds such as peracids, diacyl peroxides, hydroperoxides and the like, among which physiologically compatible acids, for example so-called edible acids, may be of particular importance as the peroxide-forming constituent. From the broad class of the activators or reducing agents, compounds such as ascorbic acids, sorbose, fructose, dextrose or other sugars, all of which are physiologically acceptable components, can be used.

Metal compounds which are suitable for stimulating and/or activating the redox system are derived, more specifically, from iron which in a per se known manner may be added to the redox systems in the form of di- and/or trivalent iron. The successful formation of a homogeneous iron-containing mixture can be safely effected, for example, by using the corresponding salts of glycolic acid and/or of lactic acid.

As has already been reported and will also be conspicuous, the variety of embodiments for the retard systems within the scope of the invention, ensures almost unlimited applicabilty of the carrier/cross-linker system to a broad range of interesting valuable materials of medicinal and generally biological activity. The active substances themselves, and the application forms thereof can be varied within wide limits. Only by way of an example are the broad limits illustrated by mixtures containing valuable materials which exhibit antibiotic action: The depot material designed to release pharmaceutical compositions, for example, may be placed into the tissue regions susceptible to become infected—for example laid thereinto—and then enclosed. However, it is also possible to apply the depot material onto open wound areas, for example wounds caused by burns or the like, and then to leave it thereon and/or to remove it at least partially and to replace it by new pharmaceutical depot material in the course of a dressing change.

The concentrations of the valuable materials in the pharmacological depot material can vary within wide limits. The dominant requirement for the substance mixtures, important in practice, is the adjustment of the desired time-retarded release of the active substance. The valuable material will in general not amount to more than 40 to 45% by weight of the retard system in its entirety. For the important sector of medicinal valuables to be applied to the human and to the animal body, valuables concentrations of from about 20 to 25% by weight and preferably of from about 10 to 15% by weight will rarely be exceeded. Highly active valuables, such as the antibiotically active substances, cytostatics, hormones and the like will generally be used in amounts of from about 0.1 to 10% by weight, and especially in amounts of from about 1 to 8% by weight, in the pharmaceutical release materials.

The valuable materials in general will be charged in an intimate admixture with at least a portion of the carrier material, in order to achieve optimum control of the release rate of the valuable material. Moreover, the considerations set forth above are applicable to the possible inhomogeneous distribution of the active material in the particular unit of the retard system. The application forms of these retard systems within the teaching according to the invention range from a powdery nature to three-dimensional bodies shaped ad libitum. The amount of the retard systems used which quantitatively is readily determined and the predetermined amount of the valuable, relative to unit volume or weight of said retard system, allows the quantified administration of the valuable materials present in the depot material.

The utilization of the teaching according to the invention in connection with administration forms less critical than for direct implantation into the living tissue, allows the concomitant use of conventional galenic auxiliary materials and/or the formulation of the retard systems of the invention into administration forms as common in practice. This may be illustrated by way of an example as follows: Pharmaceutical depot materials produced according to the invention as finely divided particulates may be formulated into tablets, suppositories, ointments and the like and, when in such form, may be introduced into the body or applied onto the body surface. Said galenic auxiliary materials in turn may contain non-retarded portions of pharmaceutical materials which will display immediate activity upon the introduction or application, which will subsequently be followed by the time-retarded period of action by the retarded release of the active substance.

In other cases, per se known auxiliary materials can be included in the composition to thereby, in a controlled manner, provide or enhance effects which are characteristic of the properties of substances adjusted within the scope of the invention. This may be exemplified by way of preparations of bioadhesive valuable materials. The covalent bond from the surface of the multi-substance mixture within the invention to the surface of the mucosa and, hence, the effect of bioadhesion, is directly caused by functional groups (carboxyl groups and/or hydroxyl groups) within the carrier material according to the invention. This effect may be further enhanced by concomitantly using known mucosa-adhesive materials as fillers in the multi-substance mixture. Suitable materials that have been well-proven in practice are, for example, in addition to carboxymethyl celluloses and (meth)acrylic acid polymers and/or copolymers, respectively, alginates, hydroxyalkylcelluloses, gelatin, pectins, polyvinylpyrrolidone, solid polyethyleneglycols and the like. Preferences to additional useful materials appear in the literature: J. D. Smart et al., "An in-vitro investigation of mucosa-adhesive materials for use in controlled drug delivery", J. Pharm. Pharmacol. 1984, 36, 295–299; as well as Kinam Park et al., "Bioadhesive polymers as platforms for oral-controlled drug delivery: method to study bioadhesion", International Journal of Pharmaceutics 19 (1984), 102–127.

The amounts of such concomitantly used auxiliary materials may vary within wide ranges and, in a particular galenic embodiment, may comprise a multiple of the substance mixtures within the scope of the invention. Then, however, what always is essential for such preparations is that a significant portion of the activity in practical use is governed by the substance combination according to the invention.

EXAMPLES

Example 1

1. Preparation and description of the resorbable waxes
a. Waxes, produced from glycolic acid/glycerol
General procedure for preparing the reaction products of glycolic acid with glycerol A three-neck flask equipped with stirrer, Claisen head and condenser ("distillation bridge") is charged with glycolic acid and glycerolo The mixture is put under an inert nitrogen gas atmosphere and heated at 150° C. The reaction is continued for 3 to 5 hours until no further water of reaction is eliminated. Then the flask is cautiously evacuated at 150° C. to 10 torro. After two more hours at these reaction conditions, the mixture is cooled to 100° C., brought to atmospheric pressure, neutralized as described above, and the product is dispensed while hot.

The compositions of the batches and the properties of the oligomers are shown in Table 1.

TABLE 1

| Oligohydroxycarboxylic acids from glycolic acid and glycerol | | |
|---|---|---|
| Example | A | B |
| Starting materials: | | |
| Glycolic acid (moles) | 8 | 9 |
| Glycerol (moles) | 1 | 1 |
| Yield: Water of reaction (%) | 100 | 99,1 |
| Consistency at room temperature | turbid, highly viscous | turbid, highly viscous |
| after neutralization | turbid, highly viscous | turbid, highly viscous |
| Viscosity at 100° C. MK-D at 20 rpm (mPa · s) | 5,000 | 10,000 |
| after neutralization | 5,000 | 10,000 |
| Degree of stringyness (cm to the break) | 2 | 2 |
| after neutralization | 7 | 7 | b. Waxes, produced from lactide and glycerol
General procedure for preparing the reaction products of lactide with glycerol Lactide {L(–)-lactide N from the company Böhringer, Ingelheim} and glycerol were heated with stirring at 195° C. in a conventional laboratory apparatus. The reaction was allowed to proceed at 195° C. for 3 hours, and after neutralization the product was dispensed while hot. A solution of Sn(II) chloride in ether had been added as a catalyst (7 ml of a solution of 2.5 g of SnCl$_2$ in 1,000 ml of ether in the reaction of 3 moles of lactide with 1 mole of glycerol).

The compositions and the properties of the oligomers are shown in Table 2.

TABLE 2

| Oligohydroxycarboxylic acids from glycerol and lactide | | |
|---|---|---|
| Example | C | D |
| Starting materials: | | |
| Glycerol (moles) | 1 | 1 |
| Lactide (moles) | 5 | 6 |
| Consistency at room temperature | clear, viscous | clear, viscous |
| after neutralization | turbid, highly viscous | turbid, highly viscous |
| Viscosity at 100° C. MK-D at 20 rpm (mPa · s) | 8,000 | 10,000 |
| after neutralization | 10,000 | 10,000 |
| Degree of stringyness (cm to the break) | about 60 | about 50 |
| after neutralization | 30 | 30 |

2. Preparation of the reactive cross-linker component
2.1 Preparation of the glycolic acid/ethylene glycol 4:1 oligomer A 25l test reactor was charged with 16.72 kg of glycolic acid and 3.41 kg of ethylene glycol. The crystal pulp was melted in an inert atmosphere under a nitrogen stream and then further heated to a maximum temperature of 145° C. to 150° C. (bottoms temperature). After the reaction had started with distillation of water, it was continued for 11 hours until no more reaction water was formed (drop in the vapor temperature to 70° C. to 73° C. at a conversion of 70%). The aqueous solution obtained upon distillation was analyzed for the quantity of distillate, the acid value (glycolic acid contents) and the water contents by the Karl Fischer method. In order to lead the reaction to completion, the mixture was carefully evacuated to 400 Torr, and the pressure was further reduced to 10 Torr within 2 hours and maintained at this level for 1 hour, in order to remove the residual water of reaction for accomplishing a quantitative conversion.

The additional amount of condensate was collected for quantification in a cold trap (cooled with dry ice and ethanol). After the total period of reaction, the mixture was cooled to 100° C. and re-pressurized to atmospheric pressure with nitrogen, and the product was dispensed while still hot. The product was directly used for the preparation of oligoglycolic acid bis-methacrylate without further purification.

2.2 Yield and mass balance

| | |
|---|---|
| Amount of Distillate | 4 222.8 g |
| Glycolic acid (from acid value = 46); 263.58 g - Ethylene glycol determined by HPLC | 263.6 g |
| Amount of water (by the Karl Fischer method) 91.6% in the distillate = = 97.7% conversion. | 3 868.1 g |

| Analytical results of the oligomer | | | |
|---|---|---|---|
| Designation | Immediately after the preparation | 1 Month old | 1 Year old |
| Batch size kg | 20 | 4.5 | 2 |
| Consistency | pastous | pastous | pastous |
| Viscosity at room temperature mPa · s (Epprecht Viscosimeter MK4) | 12,500 | 13,000 | 12,800 |

-continued

| Molecular weight | | | |
|---|---|---|---|
| $M_n$* | 438 | 455 | 454 |
| $M_w$ | 515 | 533 | 530 |
| Free glycolic acid % | 2.1 | 1.4 | 1.9 |
| Free ethylene glycol % | 0.2 | 0.2 | 0.2 |
| Saponification value | 765.4 | 754.4 | 754.0 |
| Behavior in water | | | |
| pH after 2 minutes | 3.8 | 3.8 | 3.8 |
| pH after 60 minutes | 3.4 | 3.4 | 3.4 |
| Peroxide content | negative | | |
| Analytical composition of the product glycolic acid/ethylene glycol | 3.975:1 | 3.972:1 | 3.972:1 |

*Determination of the molecular weight as GPC analysis. Since the calibration was effected with polyethylene glycol as standard, the difference between $M_n$ in theory and $M_n$ as found is due to the calibration method.

2.3 Oligoglycolic acid bis-methacrylate

Commercially available methacrylic acid (company Roehm) is newly inhibited with vitamin E according to the following procedure:

In a vacuum distillation apparatus, 15 moles (=1,291.35 g) of methacrylic acid (b.p. 163° C.) are admixed with 3.87 g (=3,000 ppm) of phenothiazine (as stabililizer); the methacrylic acid was distilled off under a strong stream of air in a water-jet vacuum. 100 ppm of vitamin E (Covitol F-1000-2, 67%, Henkel KGaA) (=139 mg/l) are placed in the receiver, and the methacrylic acid is distilled with stirring. The distillation is stopped, once 932 g of the methacrylic acid have been collected after distillation.

2.4 Course of the reaction

A three-neck flask equipped with stirrer, Claisen head and condenser ("distillation bridge") was charged with 294 g of oligoglycolic acid, 206.4 g methacrylic acid and 17.5 g of p-toluenesulfonic acid; the mixture was inhibited with 0.86 g of vitamin E (α-tocopherol). Throughout the reaction, air was passed through the mixture at a rate of at least 40 1/h.

The esterification was effected at a maximum temperature of 105° C. by removal of the water formed, until the quantity of water removed was more than 35.78 g (more than 97% conversion).

The distillation receiver was cooled with a dry ice/ethanol mixture throughout the reaction. At a maximum bottoms temperature of 105° C. and a pressure of 500 mbar the esterification time was between 12 and 14.5 hours at a total conversion of from 97 to 98.5%. The aqueous solution (as recovered from the receiver and cold trap) was sampled every 1.5 hours and was analyzed for the quantity of distillate, the acid value (methacrylic acid contents) and the water contents by the Karl Fischer method.

The water content and the amount of methacrylic acid as entrained in the distillation were calculated from the differences; after each determination, it was checked whether enough methacrylic acid was still available for the reaction. In most cases, additional 0.1 moles of methacrylic acid had to be replenished after about 7.5 or 8 hours.

Upon completion of the reaction (conversion in excess of 97%) the product was dispensed for purification.

2.5 Work-up of the reaction product

In the end of the reaction period, the product is not quite free from acid. Therefore, it was neutralized with $Ca(OH)_2$. Since in the determination of the acid value, due to the water required for the determination, the product underwent hydrolysis and a continuously increasing amount of acid was released by this reaction, it was not possible to determine the acid content by titration.

Therefore, the acid value had to be theoretically calculated.

The amount of $Ca(OH)_2$ calculated to be required for neutralization was introduced into the warm reaction product and the mixture was treated with stirring at 105° C. for 30 minutes, while 40 l/h of air under 500 mbar (gauge) were passed therethrough.

The neutralized product (highly viscous at 100° C. to 105° C.) is filtered by means of a pressurized nutsch filter and a Loeffler filter (80 NM012) at from 100° C. to 105° C. under 3 bar.

Then, the product—while still hot—was once more filtered under otherwise the same conditions through a round filter (NNG 16, medium filtering speed).

Example 2

Preparation of mixtures comprising resorbable waxes and reactive cross-linkers and the reaction thereof The reactive cross-linker (monomer in accordance with Example 1.2) is mixed with alternatively either of the two waxes according to Example 1.1a based on glycolic acid or according to Example 1.1b based on lactic acid. The properties of the mixtures are set forth in the Tables 3 through 6. For the preparation of the polymerizates, the mixtures were exposed to the radiation from a UV light source (Dr. H önle GmbH; UV ASpot 400/T; 400 W, 200/230 V) for 5 hours.

In the following Tables, "GS" refers to glycolic acid, and "EG" refers to ethyleneglycol. The substance mixtures set forth in Tables 3 and 4 were reacted under UV light without addition of a sensitizer. In contrast thereto, the substance mixtures set forth in Tables 5 and 6 were reacted with the addition of a UV sensitizer (cf. the indications in the headline of Table 5).

TABLE 3

Properties of mixtures comprising wax (glycolic acid/glycerol 9:1) and cross-linker {oligoester (GS/EG 4:1) bis-methacrylate} before and after reaction. Curing under UV light without sensitizer.

| | Mixing ratio | | | |
|---|---|---|---|---|
| No. | Wax % | Cross-linker % | Properties of the uncured mixture | Properties of the mixture after the reaction |
| 2.1 | 98 | 2 | white waxy mass, slightly tacky | waxy deformable white elastic material, slightly tacky |
| 2.2 | 97 | 3 | white waxy mass, slightly tacky | waxy deformable white elastic material, slightly tacky |
| 2.3 | 95 | 5 | white waxy mass, almost tack-free | waxy deformable white elastic material, almost tack-free |
| 2.4 | 90 | 10 | light-beige waxy mass, almost tack-free | waxy deformable light beige elastic material, almost tack-free |
| 2.5 | 80 | 20 | miscible | white waxy material, tack-free |
| 2.6 | 60 | 40 | miscible | white hard brittle material, tack-free |
| 2.7 | 40 | 60 | miscible | glassy hard material, slightly turbid |
| 2.8 | 20 | 80 | miscible | glassy hard material, slightly turbid |

TABLE 4

Properties of mixtures comprising wax (lactide/glycerol 6:1) and cross-linker {oligoester (GS/EG 4:1) bis-methacrylate} before and after reaction. Curing under UV light without sensitizer.

| No. | Mixing ratio Wax % | Cross-linker % | Properties of the uncured mixture | Properties of the mixture after the reaction |
|---|---|---|---|---|
| 2.9 | 98 | 2 | tacky tough highly stringy glass-clear mass | elastic, somewhat tacky glass-clear product |
| 2.10 | 97 | 3 | tacky tough highly stringy glass-clear mass | elastic, virtually tack-free glass-clear product |
| 2.11 | 95 | 5 | tacky tough highly stringy light-beige clear mass | slightly brittle elastic slightly turbid colorless material |
| 2.12 | 94 | 6 | tacky tough highly stringy light-beige clear mass | somewhat brittle elastic slightly turbid colorless material |
| 2.13 | 90 | 10 | tacky tough highly stringy light-yellow clear mass | hard brittle tack-free light-beige turbid material |
| 2.14 | 80 | 20 | tacky highly stringy light-yellow slightly turbid mass | hard brittle tack-free beige turbid material |
| 2.15 | 60 | 40 | slightly tacky readily fluid slightly stringy gold-colored turbid mass | hard brittle tack-free beige turbid material |
| 2.16 | 40 | 60 | miscible, liquid | hard brittle tack-free light-brown turbid material |
| 2.17 | 20 | 80 | miscible, liquid | hard brittle tack-free light-brown turbid material |

TABLE 5

Properties of mixtures comprising wax (lactide/glycerol 6:1) and cross-linker {oligoester (GS/EG 4:1) bis-methacrylate} before and after reaction. Curing under UV light with sensitizer - 4-(2-acryloyloxyethoxy)phenyl-(2-hydroxy-2-propyl)ketone (Company Merck) (4%, relative to the total composition).

| No. | Mixing ratio Wax % | Cross-linker % | Properties of the uncured mixture | Irradiation time, properties of the mixture after the reaction (UV curing) |
|---|---|---|---|---|
| 2.18 | 98 | 2 | tacky tough highly stringy glass-clear mass | 5 minutes; somewhat tacky light-yellow clear material |
|  | " | " | tacky tough highly stringy glass-clear mass | 15 minutes; deformable somewhat tacky light-yellow clear material |
|  | " | " | tacky tough highly stringy glass-clear mass | 1 hour; readily deformable almost tackfree yellow clear material |
|  | " | " | tacky tough highly stringy glass-clear mass | 5 hours; elastic somewhat brittle tackfree golden-yellow clear material |
| 2.19 | 97 | 3 | tacky tough highly stringy glass-clear mass | 5 minutes; deformable somewhat tacky light-yellow clear material |
|  | " | " | tacky tough highly stringy glass-clear mass | 15 minutes; deformable somewhat tacky light-yellow clear material |
|  | " | " | tacky tough highly stringy glass-clear mass | 1 hour; readily deformable almost tackfree yellow clear material |
|  | " | " | tacky tough highly stringy glass-clear mass | 5 hours; somewhat elastic brittle tackfree golden-yellow clear material |

TABLE 6

Properties of mixtures comprising wax (lactide/glycerol 6:1) and cross-linker {oligoester (GS/EG 4:1) bis-methacrylate} before and after reaction. Curing under UV light with sensitizer - (same as in Table 5).

| No. | Mixing ratio Wax % | Cross-linker % | Properties of the uncured mixture | Irradiation time, properties of the mixture after the reaction (UV curing) |
|---|---|---|---|---|
| 2.20 | 96 | 4 | tacky tough highly stringy glass-clear mass | 5 minutes; deformable somewhat tacky light-yellow clear material |
|  | " | " | tacky tough highly stringy glass-clear mass | 15 minutes; deformable somewhat tacky light-yellow clear material |
|  | " | " | tacky tough highly stringy glass-clear mass | 1 hour; readily deformable almost tackfree yellow clear material |
|  | " | " | tacky tough highly stringy glass-clear mass | 5 hours; slightly elastic brittle tack-free golden-yellow clear material |
| 2.21 | 95 | 5 | tacky tough highly stringy glass-clear mass | 5 minutes; deformable somewhat tacky light-yellow clear material |
|  | " | " | tacky tough highly stringy glass-clear mass | 15 minutes; deformable somewhat tacky light-yellow clear material |
|  | " | " | tacky tough highly stringy glass-clear mass | 1 hour; slightly deformable almost tackfree yellow clear material |
|  | " | " | tacky tough highly stringy glass-clear mass | 5 hours; slightly elastic brittle tack-free golden-yellow clear material |

Example 3

Samples of depot material according to the invention loaded with valuable material(s) according to the indications set forth hereinbelow are prepared, which samples were used for the determination of the release of the valuable material in an experimental model in a series of experiments.

As the valuable materials there were employed various commercially available antibiotics which are first incorporated in the carrier to form a homogeneous mixture. Then the cross-linker is added into the mixture, and the multicomponent mixture as a material layer of about 1 to 2 mm in thickness applied onto a Teflon film is exposed to UV light for several hours.

Under the working conditions employed (no sensitizer added; cooled UV lamp 500 W, irradiation time 10 hours, temperature of the multi-component mixture 28° C.) there is obtained a material the surface of which is not yet tack-free. If so desired, the mass is after-cured with an uncooled UV lamp until tack-free (15 hours; temperature 80° C.).

The following details are applicable:

Carrier material: Condensation product of lactide/glycerol in a molar ratio of 6/1

Cross-linker: Oligo(glycolic acid/ethyleneglycol 4:1) bis-methacrylate

Valuable materials: The antibiotic active substances available under the following tradenames Gentamycinsulfat®, Chloramphenicol® and Tetracyclin®.

Mixing ratios of valuables/carrier: 5% by weight and 0.1% by weight

Amount of cross-linker, relative to the valuables/carrier mixture: 3% by weight

The depot materials containing the valuable materials are prepared as follows: The oligolactic acid-based carrier material is intimately mixed with the finely divided antibiotic in the respective predetermined amounts, optionally with slightly warming the carrier material. At a temperature of 50° C., the cross-linker component is introduced so that a homogeneous mixture is formed. The composition is spread over a Teflon film to form a layer of from 1 to 2 mm in thickness and then subjected to UV curing.

Determination of the retard effect

Glass plates coated with nutrient agar were uniformly innoculated over a large area with the test bacteria employed. The material samples to be tested were brought into contact with the substrate. After two days of incubation, the inhibitory zones formed around the respective material sample to be tested were measured by determining the distance between the sample substance containing the antibiotic and the outer borderline of the inhibitory zone. Then the antibiotic-containing material samples are subjected to stepwise leaching in running tap water. After completion of each washing stage the inhibitory zones formed are determined on freshly inoculated nutrient agar plates. This operation is repeated in a number of steps until no inhibitory zones are detectable around the tested material samples.

*Staphylococcus aureus* (ATCC 6538) and *Escherichia coli* (ATCC 11229) were used as the test bacteria.

The operation of leaching with water is carried out as follows: The material to be leached is placed between to synthetic sponges. Then, using a hand spray, a uniform water flow is formed through the sponge. If required, the material samples are wrapped in a permeable thin fabric in order to exclude any material losses due to possible breakage in the course of the leaching operation.

For a better evaluation of the retard effect of the depot materials providing a sustained release of the active substance according to the invention the leaching behavior of a commercially available retard antibiotic preparation used in clinical practice is tested, in a parallel procedure under identical working conditions. The material employed here is sold by the Company Merck, Darmstadt, under the tradename of "Septopal®"-10er-Minikette. Said material of prior art is a methyl methacrylate-methyl acrylate copolymer which has been admixed with 5% by weight of gentamycin sulfate. This polymer carrier is not body-resorbable. After a surgical implantation, said material will have to be removed—usually after 5 to 7 days—or even after a period of from about 1 to 3 month(s), if necessary by surgery.

3.1 Test germ employed: *Staphylococcus aureus*

In a test series including 6 steps a retard material having the composition as set forth in the beginning of Example 3 and containing 5% by weight of gentamycin is subjected to leaching for altogether 19 days. The inhibitory zones to be formed around the respective tested material sample are determined in the beginning of the test and between the individual leaching steps in the above-described manner.

The long-term behavior of the "Septopal®" element is tested in parallel and under absolutely identical conditions.

Leaching is carried out in the following sequential steps interrupted by the determination of the inhibitory zones:

| 1st step | 4 days |
|---|---|
| 2nd step | 4 days |
| 3rd step | 3 days |
| 4th step | 2 days |
| 5th step | 3 days |
| 6th step | 3 days |

The size of the observed inhibitory zones (in mm) is summarized in the following Table 7:

TABLE 7

| | Depot material of Example 3 | "Septopal ®" |
|---|---|---|
| Inhibitory zone (mm) | 12–15 | 12–15 |
| 1st step | 8 | 8–10 |
| 2nd step | 5–7 | 5–10 |
| 3rd step | 6–8 | 7–9 |
| 4th step | 5 | 7 |
| 5th step | 6–8 | 6–8 |
| 6th step | 4 | 2–3 |

In a comparable investigation the depot material of the above-described composition according to the invention is admixed with gentamycin sulfate in a concentration of 1% by weight and is then subjected to stepwise leaching in the same manner. The inhibitory zones determined with the fresh material and after the respective steps are as follows:

| Fresh material | | 7–10 mm |
|---|---|---|
| | Days of water leaching | |
| 1st step | 4 | 5 mm |
| 2nd step | 4 | 1–2 mm |
| 3rd step | 3 | 3–5 mm |
| 4th step | 2 | 0 mm |

3.2

Comparable investigations are carried out with depot materials according to the invention which contained the following valuable materials, each in a concentration of 0.1% by weight of the antibiotic: Gentamycin sulfate, erythromycin, tetracyclin and chloramphenicol.

The leaching steps were carried out in periods of one day each, between which the size of the inhibitory zone as still observable is determined.

The blank value for the inhibitory zone (test germ: *Staph. aureus*) is about 5 to 6 mm for all of the material samples employed. The activity of the gentamycin sulfate depot material remains virtually unchanged until the third day of water leaching; then an approximately linear decrease of the size of the inhibitory zone is observed, reaching zero in the end of the 7th day of leaching. Approximately comparable is the course of the plot of the inhibitory zone size over the time for the retard material containing erythromycin. Here, however, the zero value is reached only after the end of the 8th day of leaching. Within the periods of leaching steps 5 to 7 the inhibitory zone values are improved over those of the preparation containing gentamycin sulfate.

The retard preparation containing tetracyclin shows hardly any reduction in activity after the first leaching step; then, however, a rapid activity loss occurs. The preparation containing chloramphenicol shows an activity loss less than 50% of the initial value already in the end of the 1st day of water leaching.

If, however, now the concentration of the active ingredient is increased to 5% by weight and an oligomer based on glycerol/glycolic acid/lactic acid in a molar ratio of 1/2/10 is employed, then the blank value of the inhibitory zone produced by the tetracyclin-containing preparation (42 mm) is just comparably insignificantly decreased by about 10 units (31 mm) within a period of 8 days of water leaching. Somewhat higher within said period is the activity loss of the material samples containing, on the one hand, gentamycin sulfate and, on the other hand, erythromycin as the antibiotic. Nevertheless, also here an antibiotic activity of more than 50% of the blank value is retained.

Corresponding investigations carried out on nutrient substrates with *E. coli* as the test germ confirm the retard effect in the release of the antibiotic substances within the meaning of the teaching according to the invention.

What is claimed is:

1. A sustained release dosage form of biologically active materials which comprises: (1) a dosage effective amount of the biologically active material; (2) a carrier comprised of an oligoester of a hydroxycarboxylic acid having from 2 to 6 carbon atoms; and, (3) a crosslinked crosslinker selected from the group consisting of oligoesters of hydroxycarboxylic acids having from 2 to 6 carbon atoms and at least 2 olefinically unsaturated groups per oligoester molecule and esters of hydroxycarboxylic acids having from 2 to 6 carbon atoms and at least 2 olefinically unsaturated groups wherein said esters are not oligoesters.

2. The dosage form of claim 1 wherein said oligoester is an oligoester of a hydroxycarboxylic acid having from 2 to 4 carbon atoms.

3. The dosage form of claim 2 wherein said hydroxycarboxylic acid comprises at least one of lactic acid and glycolic acid.

4. The dosage form of claim 1 wherein said crosslinker is an oligoester of glycerol and lactic acid and said olefinically unsaturated groups comprise residues of (meth)acrylic acid.

5. The dosage form of claim 4 wherein said crosslinker is comprised of three (meth)acrylic acid ester groups.

6. The dosage form of claim 4 wherein the crosslinker comprises a composition formed by reaction of a mixture with a mole ratio of glycerol/lactic acid/(meth)acrylic acid of 1/4/3.

7. The dosage form of claim 4 wherein the crosslinker is in a mixture wherein the mixture comprises oligesters having olefinically unsaturated groups wherein the average number of olefinically unsaturated groups of all the oligoester molecules with olefinic unsaturation in the mixture is from about 2 to about 3.

8. The dosage form of claim 1 wherein the molecular weight of said oligoester of component (2) is from about 200 to about 5,000.

9. The dosage form of claim 8 wherein said molecular weight is from about 300 to about 2,000.

10. The dosage form of claim 1 wherein said oligoester of component (2) is the reaction product of an oligomer of lactic acid and glycerol having a molecular weight of from about 200 to about 1,500.

11. The dosage form of claim 10 wherein the crosslinker is in a mixture wherein the mixture comprises oligoesters having olefinically unsaturated groups wherein the average number of olefinically unsaturated groups of all the oligoester molecules with olefinic unsaturation in the mixture is greater than 1.

12. The dosage form of claim 1 wherein said crosslinked crosslinker is present in the amount of from about 1% to about 20% by weight of the combined weight of said carrier and said crosslinker.

13. The dosage form of claim 12 wherein said crosslinked crosslinker is present in the amount of less than about 10% by weight of the combined weight of said carrier and said crosslinker.

14. The dosage form of claim 1 wherein said composition is comprised of alternating first and second layers wherein said first layer is comprised of said biologically active material and said carrier and said second layer is comprised of said crosslinked crosslinker.

15. The dosage form of claim 14 wherein said crosslinker is in a mixture wherein the mixture comprises oligoesters having olefinically unsaturated groups comprising at least one cross-linker selected from the group consisting of oligoesters of lactic acid and oligoesters of glycolic acid wherein the average number of olefinically unsaturated groups of all the oligoester molecules with olefinic unsaturation in the mixture is from about 2 to about 4.

16. The dosage form of claim 15 wherein said average number of olefinically unsaturated groups is from about 2 to about 3.

17. The dosage form of claim 14 wherein said crosslinker is an oligoester containing residues selected from the group consisting of (a) residues of lactic acid, ethylene glycol, and methacrylic acid; (b) residues of lactic acid, glycerol, and methacrylic acid; (c) residues of glycolic acid, ethylene glycol, and methacrylic acid; and (d) residues of glycolic acid, glycerol, and methacrylic acid.

18. The dosage form of claim 14 wherein said oligoester of the hydroxycarboxylic acid has a molecular weight of from about 200 to about 5,000.

19. A process for making the dosage form of claim 1 comprising mixing a first composition comprised of said carrier and said biologically active substance with said crosslinker and crosslinking said crosslinker.

20. A composition for forming the sustained release dosage form of claim 1 which comprises: (1) a dosage effective amount of the biologically active material; (2) a carrier comprised of an oligoester of a hydroxycarboxylic having from 2 to 6 carbon atoms; and (3) a crosslinker comprised of at least one member selected from the group consisting of oligoesters of hydroxycarboxylic acids having from 2 to 6 carbon atoms and having at least two olefinically unsaturated groups per oligoester molecule and esters of hydroxycarboxylic acids having from 2 to 6 carbon atoms and at least 2 olefinically unsaturated groups wherein said esters are not oligoesters.

21. A dosage form comprising: (1) an inner core which is comprised of an effective amount of a biologically active substance and a carrier comprised of an oligoester of a hydroxycarboxylic acid having from 2 to 6 carbon atoms and, (2) an outer layer comprised of a crosslinked member selected from the group consisting of oligoesters of hydroxycarboxylic acids having from 2 to 6 carbon atoms comprised of at least 2 olefinically unsaturated groups per oligoester molecule, esters of hydroxycarboxylic acids having from 2 to 6 carbon atoms and at least 2 olefinically unsaturated groups wherein said esters are not oligoesters, deposited on the surface of said inner core.

* * * * *